(12) United States Patent
Ehman et al.

(10) Patent No.: US 9,149,204 B2
(45) Date of Patent: Oct. 6, 2015

(54) FLEXIBLE PASSIVE ACOUSTIC DRIVER FOR MAGNETIC RESONANCE ELASTOGRAPHY

(75) Inventors: Richard L. Ehman, Rochester, MN (US); Jun Chen, Rochester, MN (US); Phillip J. Rossman, Rochester, MN (US)

(73) Assignee: MAYO FOUNDATION FOR MEDICAL EDUCATION AND RESEARCH, Rochester, MN (US)

( * ) Notice: Subject to any disclaimer, the term of this patent is extended or adjusted under 35 U.S.C. 154(b) by 0 days.

(21) Appl. No.: 13/453,681

(22) Filed: Apr. 23, 2012

(65) Prior Publication Data

US 2012/0271150 A1 Oct. 25, 2012

Related U.S. Application Data

(60) Provisional application No. 61/478,295, filed on Apr. 22, 2011.

(51) Int. Cl.
*A61B 5/055* (2006.01)
*A61B 5/00* (2006.01)
*A61B 8/08* (2006.01)

(52) U.S. Cl.
CPC ............... *A61B 5/055* (2013.01); *A61B 5/0051* (2013.01); *A61B 8/485* (2013.01)

(58) Field of Classification Search
USPC .................. 600/407, 410, 411; 324/309, 322
See application file for complete search history.

(56) References Cited

U.S. PATENT DOCUMENTS

| | | | |
|---|---|---|---|
| 5,010,878 | A | 4/1991 | Kline et al. |
| 5,592,085 | A | 1/1997 | Ehman |
| 5,606,971 | A | 3/1997 | Sarvazyan |
| 5,810,731 | A | 9/1998 | Sarvazyan et al. |
| 5,952,828 | A | 9/1999 | Rossman et al. |
| 5,977,770 | A | 11/1999 | Ehman |
| 6,037,774 | A | 3/2000 | Felmlee et al. |
| 6,486,669 | B1 | 11/2002 | Sinkus et al. |
| 7,002,347 | B2 | 2/2006 | Feiweier et al. |
| 7,034,534 | B2 | 4/2006 | Ehman et al. |
| 7,278,963 | B2 | 10/2007 | Schneider et al. |
| 7,307,423 | B2 | 12/2007 | Ehman et al. |

(Continued)

OTHER PUBLICATIONS

Bensamoun, et al., Determination of Thigh Muscle Stiffness Using Magnetic Resonance Elastography, Journal of Magnetic Resonance Imaging, 2006, 23:242-247.

*Primary Examiner* — Joel F Brutus
(74) *Attorney, Agent, or Firm* — Quarles & Brady, LLP

(57) ABSTRACT

A flexible passive acoustic driver for use in an acoustic driver system which applies an oscillating stress to a subject undergoing a magnetic resonance elastography (MRE) examination which includes receiving acoustic pressure waves from an active driver through a tube and imparts pressure waves to a subject of an imaging procedure. In one configuration, the passive driver includes a flexible bag that forms the walls of an acoustic cavity, and a structure filling material located inside the acoustic cavity provides support for the flexible bag. The flexible bag conforms to the shape of the subject and may be held in place by an elastic band. The passive driver can have an integrated or detachable non-active push-on compartment which is rigid or semi-flexible to improve the human-driver mechanical coupling and the driver energy efficiency of converting acoustic pressure to mechanical vibration applied to a subject.

20 Claims, 5 Drawing Sheets

(56) References Cited

U.S. PATENT DOCUMENTS

| | | |
|---|---|---|
| 2003/0149359 A1 | 8/2003 | Smith |
| 2003/0210811 A1 | 11/2003 | Dubowsky et al. |
| 2005/0018868 A1 | 1/2005 | Chick et al. |
| 2005/0025330 A1* | 2/2005 | Saiki et al. .................... 381/388 |
| 2005/0157900 A1 | 7/2005 | Litovsky et al. |
| 2005/0196012 A1 | 9/2005 | Babb et al. |
| 2005/0270029 A1* | 12/2005 | Ehman et al. ................ 324/318 |
| 2006/0012367 A1 | 1/2006 | Meaney et al. |
| 2006/0189868 A1 | 8/2006 | Gleich et al. |
| 2006/0241432 A1 | 10/2006 | Herline et al. |
| 2007/0113843 A1* | 5/2007 | Hughes ................... 128/200.24 |
| 2007/0156156 A1 | 7/2007 | Badie |
| 2009/0299168 A1* | 12/2009 | Ehman et al. ................. 600/410 |
| 2010/0005892 A1 | 1/2010 | Ehman et al. |
| 2011/0264090 A1* | 10/2011 | Shadduck et al. .............. 606/41 |
| 2011/0288639 A1* | 11/2011 | Trilokekar et al. ................ 623/8 |

* cited by examiner

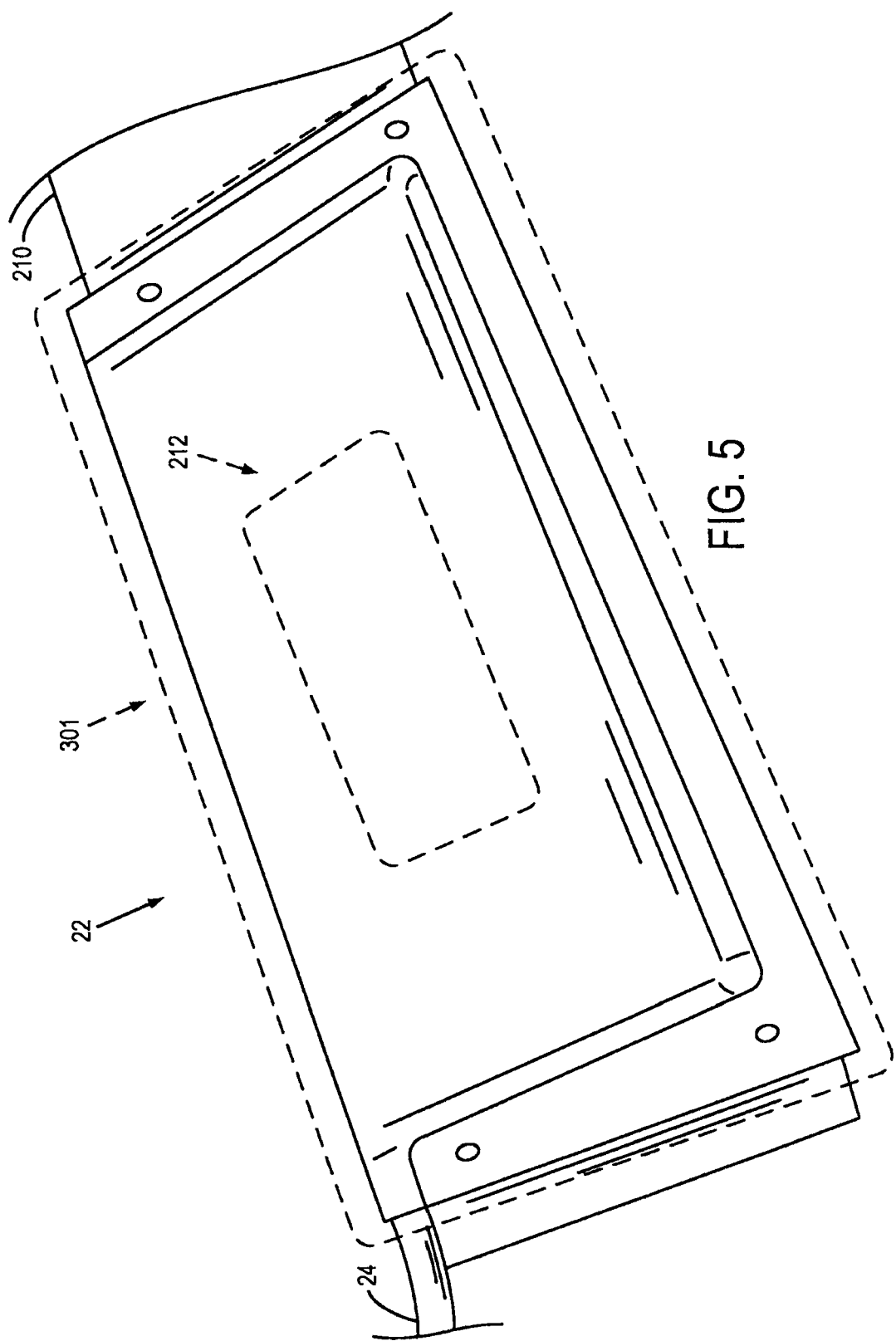

FLEXIBLE PASSIVE ACOUSTIC DRIVER FOR MAGNETIC RESONANCE ELASTOGRAPHY

CROSS-REFERENCE TO RELATED APPLICATIONS

This application claims the benefit of U.S. Provisional Patent Application No. 61/478,295 filed Apr. 22, 2011, the disclosure of which is hereby incorporated by reference in its entirety.

STATEMENT REGARDING FEDERALLY SPONSORED RESEARCH

This invention was made with government support under EB001981 awarded by the National Institutes of Health. The government has certain rights in this invention.

FIELD OF THE INVENTION

The field of the invention is nuclear magnetic resonance imaging methods and systems. More particularly, the invention relates to devices for implementing magnetic resonance elastography (MRE).

BACKGROUND OF THE INVENTION

The physician has many diagnostic tools at his or her disposal which enable detection and localization of diseased tissues. These include x-ray systems that measure and produce images indicative of the x-ray attenuation of the tissues and ultrasound systems that detect and produce images indicative of tissue echogenicity and the boundaries between structures of differing acoustic properties. Nuclear medicine produces images indicative of those tissues which absorb tracers injected into the patient, as do PET scanners and SPECT scanners. And finally, magnetic resonance imaging (MRI) systems produce images indicative of the magnetic properties of tissues. It is fortuitous that many diseased tissues are detected by the physical properties measured by these imaging modalities, but it should not be surprising that many diseases go undetected.

Historically, one of the physician's most valuable diagnostic tools is palpation. By palpating the patient, a physician can feel differences in the compliance of tissues and detect the presence of tumors and other tissue abnormalities. Unfortunately, this valuable diagnostic tool is limited to those tissues and organs which the physician can feel, and many diseased internal organs go undiagnosed unless the disease happens to be detectable by one of the above imaging modalities. Tumors (for example, of the liver) that are undetected by existing imaging modalities and cannot be reached for palpation through the patient's skin and musculature, are often detected by surgeons by direct palpation of the exposed organs at the time of surgery. Palpation is the most common means of detecting tumors of the prostate gland and the breast, but unfortunately, deeper portions of these structures are not accessible for such evaluation. An imaging system that extends the physician's ability to detect differences in tissue compliance throughout a patient's body would extend this valuable diagnostic tool.

It has been found that MR imaging can be enhanced when an oscillating stress is applied to the object being imaged in a method called MR elastography (MRE). The method requires that the oscillating stress produce shear waves that propagate through the organ, or tissues to be imaged. These shear waves alter the phase of the MR signals, and from this the mechanical properties of the subject can be determined. In many applications, the production of shear waves in the tissues is merely a matter of physically vibrating the surface of the subject with an electromechanical device such as that disclosed in U.S. Pat. No. 5,592,085. For example, shear waves may be produced in the breast and prostate by direct contact with the oscillatory device. Also, with organs like the liver, the oscillatory force can be directly applied by means of an applicator that is inserted into the organ.

A number of driver devices have been developed to produce the oscillatory force needed to practice MRE. As disclosed in U.S. Pat. Nos. 5,977,770, 5,952,828, 6,037,774, and 6,486,669, these typically include a coil of wire through which an alternating current flows. This coil is oriented in the polarizing field of the MRI system such that it interacts with the polarizing field to produce an oscillating force. This force may be conveyed to the subject being imaged by any number of different mechanical arrangements. Such MRE drivers can produce large forces over large displacement, but they are constrained by the need to keep the coil properly aligned with respect to the polarizing magnetic field. In addition, the current flowing in the driver coil produces a magnetic field which can alter the magnetic fields during the magnetic resonance pulse sequence resulting in undesirable image artifacts.

Another approach is to employ piezoelectric drivers as disclosed in U.S. Pat. Nos. 5,606,971 and 5,810,731. Such drivers do not produce troublesome disturbances in the scanner magnetic fields when operated, but they are limited in the forces they can produce, particularly at larger displacements. Piezoelectric drivers can also be oriented in any direction since they are not dependent on the polarizing magnetic field direction for proper operation.

Yet another approach is to employ an acoustic driver system as described in U.S. Pat. Nos. 7,034,534, 7,307,423, and U.S. Pat. Application Publication 2009/0299168. The acoustic driver system includes an active driver located remotely from the MRI system and acoustically coupled by a tube to one or more passive drivers positioned on the subject being imaged. The passive drivers do not disturb the magnetic fields and may be oriented in any direction.

There are clinical situations where existing passive drivers cannot reliably or comfortably be positioned to adequately vibrate, or illuminate, tissues in the region of interest. Existing MRE passive drivers, such as the prior art driver 100 shown in FIG. 3, are rigid and cylindrical and consequently do not always conform well to the anatomical shape of a subject. As a result, incomplete surface area contact between the subject and the passive driver causes reduced MRE driver efficiency and a reduced MRE signal. These problems are most problematic in, but not limited to, situations where the mass loading of the region of interest is high or where there is a need to vibrate tissue deeper within the body.

Additionally, many of the flexible passive drivers which have been disclosed in U.S. 2009/0299168 require a rigid back plate in order to impart motion to the subject. While this rigid back plate may impart motion to the subject with high efficiency, there are many situations where the rigid back plate can interfere with subject placement and comfort, such as when a subject is lying upon the driver.

SUMMARY OF THE INVENTION

The present invention provides a passive acoustic driver that receives acoustic pressure waves through a tube and imparts pressure waves to a subject of an imaging procedure. In one implementation, the passive driver includes a flexible bag forming walls of an acoustic cavity, and engages the subject of the examination. Also, the driver includes an intake pipe which is connectable to the tube and conveys acoustic pressure waves into the acoustic cavity, and a structure filling material located inside the acoustic cavity provides support for the flexible bag. The flexible bag is designed to conform to the shape of the subject and may be coupled with an elastic band to be affixed to the subject This flexible passive acoustic driver is patient-friendly, comfortable and safe.

In another implementation, the present invention is an acoustic driver system for producing a stress on a subject undergoing an imaging procedure. The system includes an active driver located remotely from the subject that includes a diaphragm operable to produce oscillating acoustic energy by actuating the diaphragm. The system includes a passive driver positioned on a surface of the subject. The passive driver has a flexible enclosure which defines an enclosed chamber when placed on the subject. The flexible enclosure has a port for receiving acoustic energy. The active driver is acoustically coupled to the passive driver such that the surface of the subject upon which the flexible enclosure rests vibrates in response to the acoustic energy produced by the active driver.

One aspect of the invention is to improve the patient comfort when using a passive acoustic driver. The driver may flex to follow the general contour of the subject being imaged. The driver compresses as needed to uniformly distribute the force holding the passive driver in place. Pressure points are thus avoided.

The foregoing and other advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

FIG. 5 is a picture of one configuration for the flexible passive driver.

DETAILED DESCRIPTION OF THE INVENTION

Figure 1:
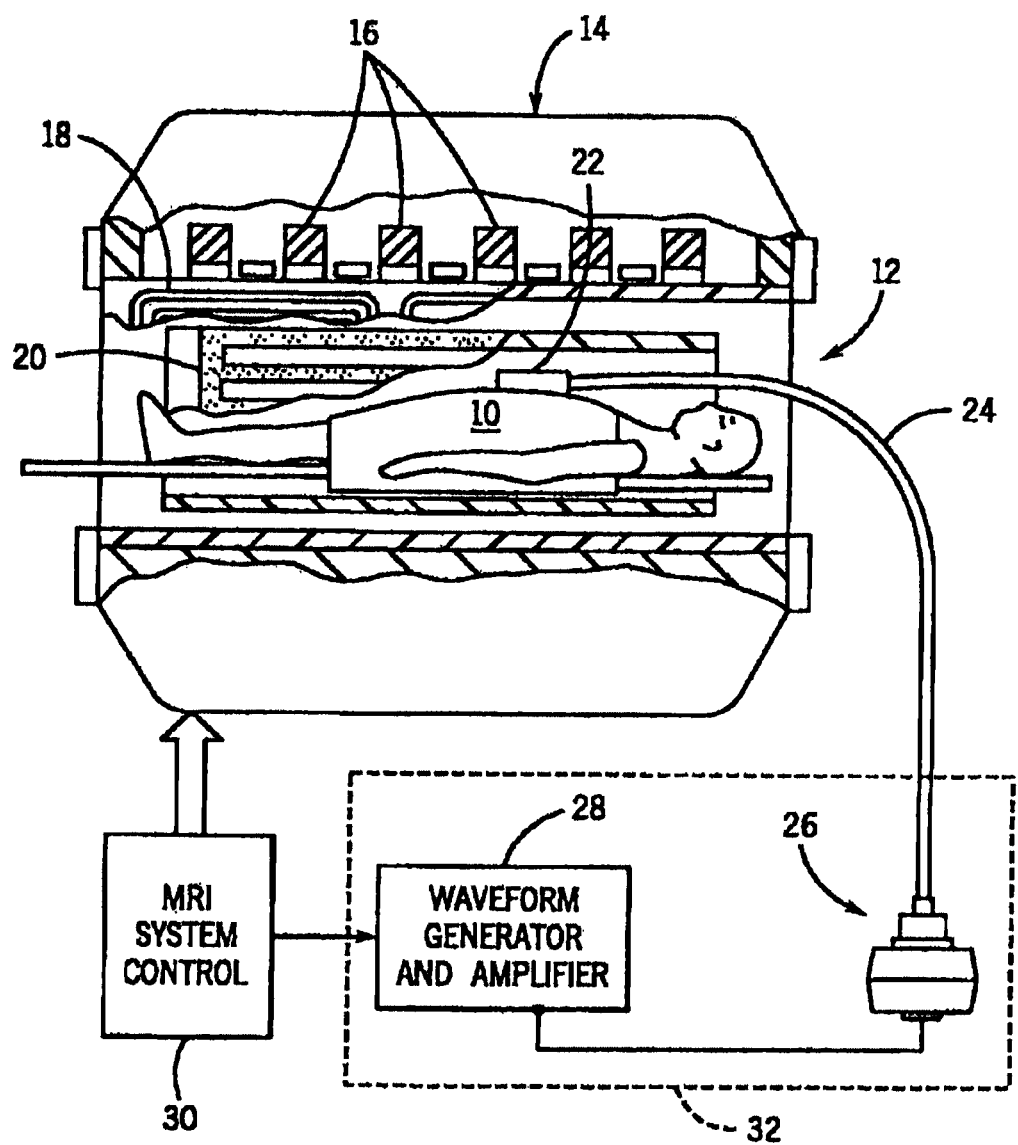
FIG. 1 is a pictorial representation of an MRI system which employs an implementation of the present invention.

The present invention is employed in a system such as that described in the previously-cited U.S. Pat. No. 5,592,085, which provides a means for measuring the strain in gyromagnetic materials, such as tissues, using MR methods and apparatus. The present invention may also be employed with other medical imaging modalities including, but not limited to, ultrasound. Referring to FIG. 1, a subject to be examined 10 is placed in the bore 12 of an MRI system magnet 14 and is subjected to magnetic fields produced by a polarizing coil 16, gradient coils 18 and an RF coil 20 during the acquisition of MR data from a region of interest in the subject 10. The homogeneity of these magnetic fields is important and any objects placed in the bore 12 must be carefully constructed of materials that will not perturb them.

The present invention is a passive driver system that may be placed on the subject 10 and energized to produce an oscillating, or vibratory, stress. It includes a passive driver 22 positioned over the region of interest in the subject 10 and connected by means of a tube 24 to a remotely located active acoustic driver 26. The active driver 26 is remote from the bore 12 of the magnet 14 in the sense that it is positioned away from the strong magnetic fields produced by the magnet 14 where its operation is not impeded by those fields, and where its operation will not perturb the MRI system magnetic fields. The active driver 26 is electrically driven by a waveform generator and amplifier 28, which in turn is controlled by a pulse sequencer in the MRI system control 30. The MRI system control 30 directs the MRI system to perform an MRE scan by driving the RF coil 20 and the gradient coils 18 in the magnet assembly 14 to perform a series of pulse sequences, while enabling the waveform generator 28 at the proper moment during each pulse sequence to apply an oscillatory stress to the subject 10 as described in the previously-cited U.S. Pat. No. 5,592,085. The active driver 26 and the waveform generator and amplifier 28 may be housed together in a manually portable unit, denoted with a dashed line 32.

Using the above-described system, the physical properties of tissue can be measured using MR elastography (MRE) by applying the stress (for example, tension, pressure, or shear) and observing the resulting strain (for example, elongation, compression, rotation). By measuring the resulting strain, elastic properties of the tissue such as Young's modulus, Poisson's ratio, the shear modulus, and the bulk modulus can be calculated. By applying the stress in all three dimensions and measuring the resulting strain, the elastic properties of the tissue can be defined.

By observing the rate at which the strain decreases as a function of distance from the stress producing source, the attenuation of the strain wave can be estimated. From this, the viscous properties of the gyromagnetic medium may be estimated. The dispersion characteristics of the medium can be estimated by observing the speed and attenuation of the strain waves as a function of their frequency. Dispersion is potentially a very important parameter for characterizing tissues in medical imaging applications.

Figure 2:
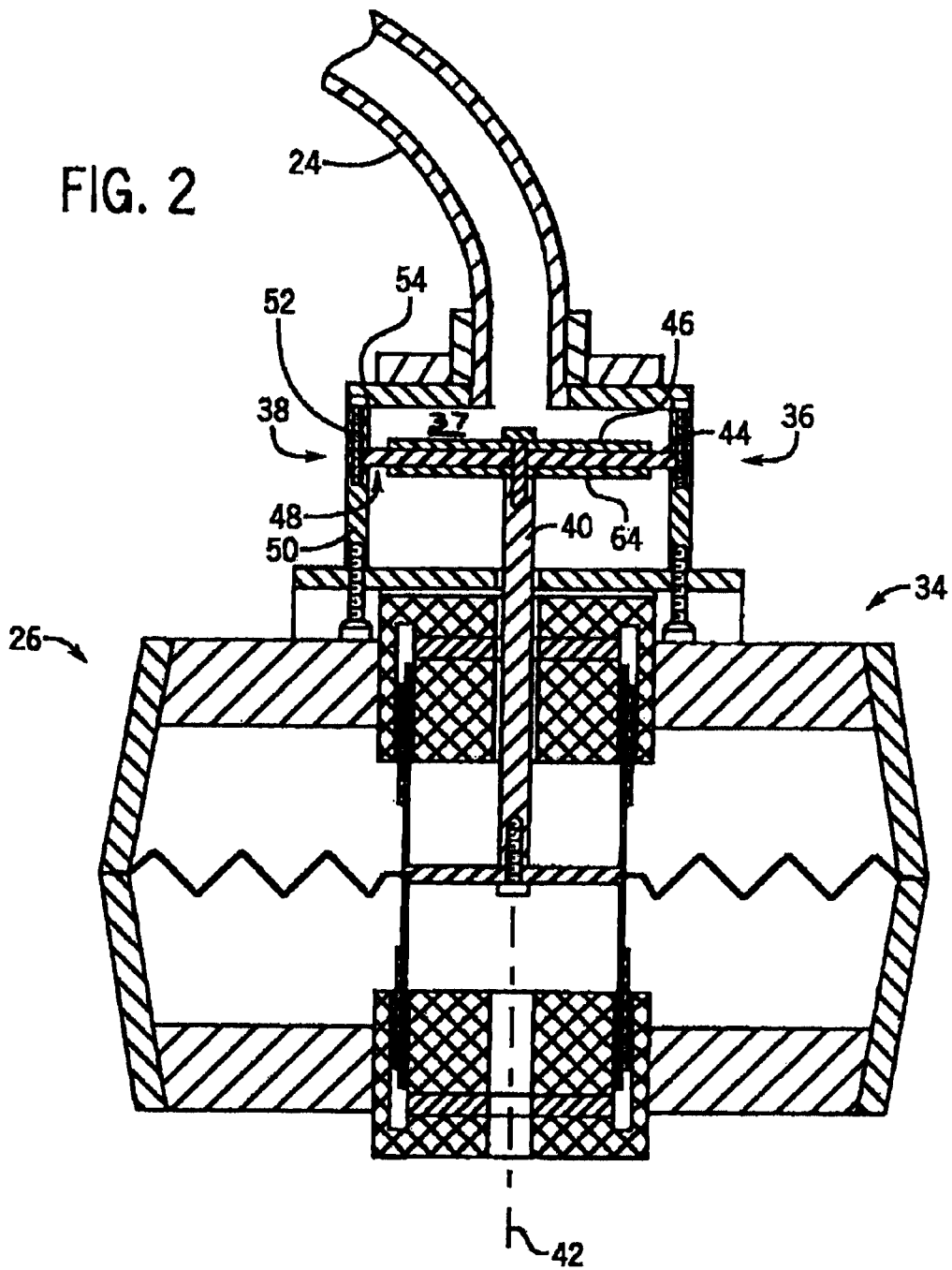
FIG. 2 is a cross-sectional view of an active driver used in the MRI system of FIG. 1.

Referring to FIG. 2, while an active acoustic driver such as that disclosed in the above-cited U.S. Pat. Nos. 7,034,534, and 7,307,423, and U.S. Patent Application Publication Nos. US2009/0299168 and US201 0/0005892, can be used with the present invention, an active driver 26 includes a discrete, high-powered linear motor 34 and a rigid cylindrical housing 36 defining an acoustical chamber 37. Acoustic pressure waves are produced by the active driver 26 when the motor 34 actuates a stiffened diaphragm 38 contained within the chamber 37. The linear motor 34 converts an alternating current from the waveform generator and amplifier 28 into a reciprocating linear motion. The linear motion is translated by a drive rod 40 that extends along a motor axis 42. The drive rod 40 is attached to the diaphragm 38 located within the chamber 37.

The diaphragm 38 is comprised of a silicone rubber circular piece 44 sandwiched between two smaller diameter plastic stiffening plates 46 to form a rigid portion having a surrounding compliant perimeter 48. A portion of the compliant perimeter 48 is secured to the housing 36 between a lower chamber section 50 and an upper chamber section 52, thereby forming an air-tight seal within the chamber 37. The active driver 26 further includes a ported cap 54 to acoustically couple the tube 24 to the chamber 37.

When repeatedly stroked by the drive rod 40, the diaphragm 38 produces oscillating acoustic, or pressure, waves. This acoustic energy is transmitted via the tube 24 to the passive driver 22. The magnitude and frequency of the diaphragm 38 displacement and hence the magnitude and frequency of the pressure waves, is set by the waveform generator and amplifier 28.

The tube 24 is made of a material which is flexible, yet inelastic. The flexibility enables it to be fed along a winding path between the subject 10 in the magnet 14 and the remote site of the active driver 26. In one configuration, the tube 24 is twenty feet long and has an inner diameter of one inch. It is made of a clear vinyl material sold under the trademark TYGON and has a wall thickness of approximately one-eighth inch. TYGON is a registered trademark of Norton Company of Worchester, Mass. Alternatively, tube 24 includes a PVC tube with a reinforced wall having an inside diameter of approximately % inches. The tube 24 is inelastic such that it does not expand in response to the variations in air pressure caused by the acoustic energy it conveys. As a result, the acoustic energy is efficiently conveyed from the active driver 26 to the passive driver 22.

Figure 4A:
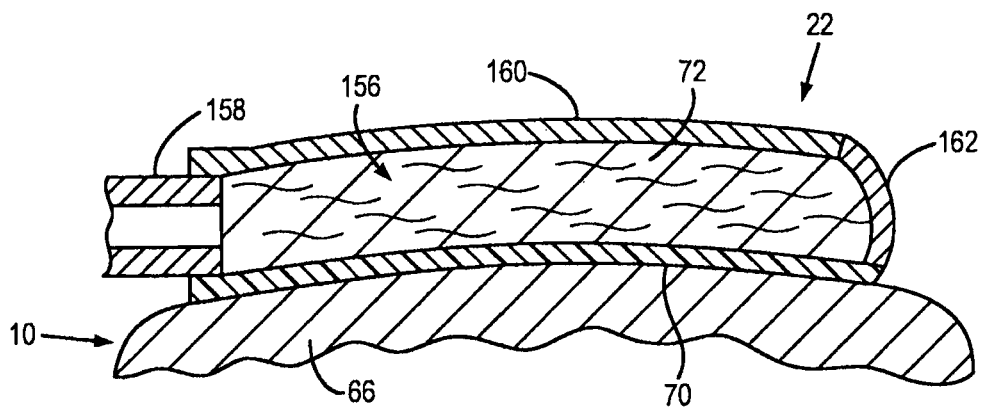
FIGS. 4A and B are cross-sectional views of implementations of the flexible passive driver showing the driver on a subject and flexed accordingly.
Figure 4B:
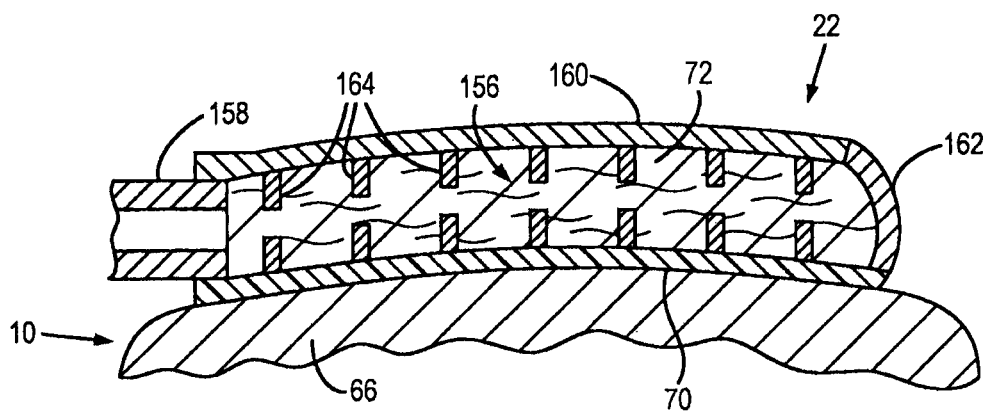

Referring to FIGS. 4A and 4B, the flexible passive acoustic driver 22 includes a flexible material or membrane 70. The passive driver 22 further includes a thin chamber 156 defined by an end wall 160, side walls 162, and the membrane 70. The end wall 160 may be formed from a flexible material such as woven fabric, thin polycarbonate plastic, styrofoam, foam rubber, a non-stretching material mesh, or the like. The side walls 162 may be made of the same or similar material. The membrane 70 may also be made from the same or similar material. The chamber 156 is filled with a highly porous yet flexible material 72, such as a loose, woven fabric, a polyfiber material, a 3M Scotch-Brite pad material (Non-Woven Web Material in Sheet Form for Cleaning and Finishing All Types of Surfaces), or a material such as used in a furnace or air filter.

The material used for the walls 160 and 162 and the membrane 70, may generally be any material which is flexible, but, preferably, not stretchable, and does not fold onto itself easily. In some configurations, the material has a build-in two-dimensional mesh of thread. This kind of material allows for the driver 22 to conform to the subject 10 and for motion to be imparted to the subject 10 repeatedly, reliably, and efficiently, without the driver 22 undesirably deforming upon receiving the acoustic pressure waves from the active driver 26, which would be highly inefficient at imparting vibrational energy to a subject 10.

The material 72 which fills the chamber 156 may be any material which can support and maintain separation between the driver walls 160 and 162 and the membrane 70. This three-dimensional filling material 72 is also preferably porous to facilitate free air flow inside the driver 22. Rods or baffles 164 (FIG. 4B) made of any similarly MR compatible material may be disposed within the chamber 156 and surrounded by the three-dimensional filling material 72 in order to aid in supporting the driver walls 160 and 162 and controlling the flow of air. Such rods or baffles 164 may be held in place with double sided tape, or some other form of adhesive, to the inside of the driver walls 160 and/or 162.

The flexible membrane 70 is placed against the skin 66 of the subject 10 and, along with the entire passive driver 22, conforms to the shape of the subject 10. The diaphragm 70 vibrates in response to the acoustic energy received through the tube 24 and an intake port 158. The vibrations apply an oscillating stress to the skin 66 of the subject 10 which is conveyed into the region of interest as shear waves. The material 72 in the chamber 156 maintains an appropriate spacing between the skin 66 and the end wall 160 and does not impede the pressure waves traveling therethrough.

Referring to FIG. 5, one configuration is for the flexible driver to take the form of, for example, a 10 in. by 6.5 in. by 0.5 in. three-dimensional structure filled with a three-dimensional structure filling material 72. However, the driver 22 may be made thinner and longer in order to facilitate placement on the sternum or elsewhere. The flexible driver 22 can be made in different forms and shapes according to different anatomy, organs, or patient body shape, in order to improve the mechanical coupling between the driver 22 and the subject 10. The flexible driver may be particularly useful to vibrate brain, breast, liver, kidney, muscle and vessels. The shape and curvature of the flexible driver 22 may be appropriate for use in a head coil, or other birdcage shaped coil. That is, one or more flexible drivers 22 may be situated between the subject 10 and the birdcage coil being utilized for imaging a specific anatomic feature. For example, two flexible drivers 22 may be placed against the back of the subject's head and under a head coil to conduct brain imaging.

A strap or band 210 may connect to the walls of the driver 22 and be used to hold the driver 22 against the subject 10. The strap 210 may also include a non-elastic material such as a fabric including a hook-and-loop fastener, or an elastic material such as neoprene. The strap 210 may be disposed around the subject 10 and the driver 22 is held between the subject 10 and the strap 210. For relatively thin subjects, the driver 22 may be located on a relatively flat surface. In this case, the driver 22 may be relatively thick or may have additional material located above the driver 22 where the strap 210 is connected. As such, the strap 210 may facilitate better contact between the subject 10 and the driver 22 than other configurations.

In this configuration, a non-active push-on compartment 212 that does not vibrate is included. This compartment 212 improves the mechanical coupling between the driver 22 and subject 10. This compartment 212 is added to the back of the flexible driver 22, not between the flexible driver 22 and the subject 10. When the push-on compartment 212 and flexible driver 22 are wrapped on the subject 10 by the strap 210, the compartment 212 pushes and supports the flexible driver 22 against the subject 10; therefore, the compartment 212 increases the mechanical coupling. As noted above, the flexible driver 22 itself could be made thicker in order to improve the mechanical coupling; however the efficiency of the pressure-to-vibration energy conversion and the frequency bandwidth are highly decreased by the increased volume of the flexible driver 22. For renal transplanted subjects, this driver 22 is especially useful for measuring the renal stiffness, because it is soft, comfortable and safe; it has high frequency BW, high pressure-to-vibration conversion efficiency, and high mechanical coupling.

The non-active push-on compartment 212 can be of any size, may be larger or smaller than the active portion of the flexible driver 22, and can be inside or outside of the active portion of the driver 22. The non-active push-on compartment 212 is rigid or semi-flexible so that it can improve the energy efficiency of converting acoustic pressure to mechanic vibration of the driver 22. The rigid or semi-flexible push-on compartment 212 restrains the vibration of one driver surface. As such, the compartment 212 reflects acoustic pressure to a surface on the opposite side of the driver 22 in contact with the subject 10, resulting in increased vibration amplitude applied to the subject 10.

The active portion of the flexible driver 22 and the non-active push-on compartment 212 can be integrated into one component or separated depending on the application in which the driver 22 is used. For some applications, like brain imaging using a head coil as described above, a single soft driver is placed between the subject's head and the coil, and the push-on compartment 212 may be omitted because the coil itself acts as a push-on compartment for the flexible driver. For some applications, like large organ imaging (for example, liver and spleen imaging), a large semi-flexible push-on compartment 301, which has a similar size as the active portion of the flexible driver is used to improve human-driver mechanical coupling and energy efficiency. For some applications, like small organ imaging (for example, kidney or transplanted kidney imaging), the small-size push-on compartment 212 is rigid and is disposed on the back of the active portion of the flexible driver 22. In these applications, the push-on compartment 212 improves energy efficiency and mechanical coupling.

Regardless of size and application, the non-active compartment may be integrally connected to the active portion of the flexible driver 22, or the non-active compartment may be detachable. Materials for the non-active compartment may include, for example, polycarbonates, thermoplastics, woods, foams or other solid MR-compatible materials. In addition, the non-active compartment may be sterilizable with normal sterilization methods or kept clean with a cloth case. Alternatively the non-active compartment may be disposable.

In some configurations, the flexible passive driver 22 may be sized to cover two or more organs or regions of interest. For example, if images of both the spleen and liver are desired, the driver 22 could be large enough to cover the torso over both organs and thereby impart vibrational energy into both organs for imaging.

In some configurations, the flexible passive driver 22 extends entirely around the subject 10, such that an arm, leg, torso, or any other part of the body is entirely encircled by a flexible driver 22 so that a strap or band 210 is no longer required to hold the driver 22 against the subject 10. In these configurations, the flexible driver 22 itself would maintain constant contact with the subject 10.

In these configurations, the passive driver 22 forms a tight band around the subject's appendage and applies an oscillating constrictive force to the appendage in response to the acoustic energy delivered through the flexible tube 24 from the active driver 26. Furthermore, the passive driver 22 may be made of a fabric material which expands and contracts in response to the applied acoustic energy. Expansion of the flexible driver 22 tightens or constricts around the subject's torso, for example, and contraction of the diameter loosens the grip around the torso. This oscillating constrictive force applied around an appendage has been found to produce high-quality MRE images of structures in the appendage.

Depending upon the system configuration, the passive driver 22 may be formed in any number of turns around the subject's torso in these configurations. In some cases, a single turn may be sufficient to transfer acoustic energy into the subject's torso for medical imaging. Other implementations, however, may call for many turns formed around the torso to ensure sufficient delivery of acoustic energy from the passive driver into the torso.

Figure 6A:
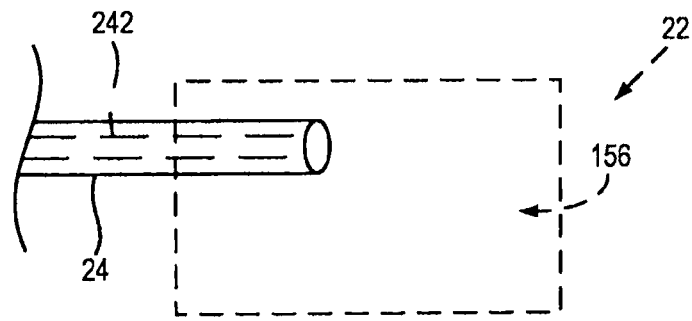
FIGS. 6 A, B, and C are cross-sectional views of alternate configurations for the flexible passive driver.
Figure 6B:
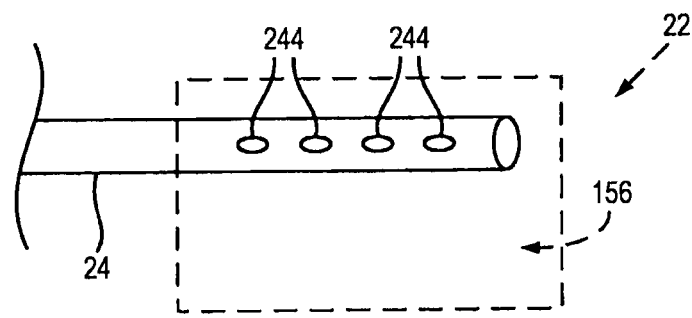
Figure 6C:
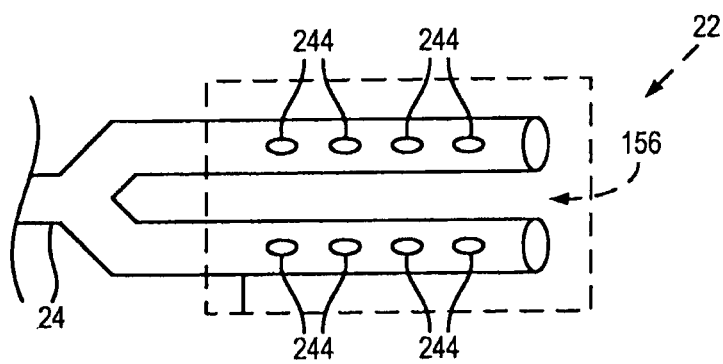

Referring to FIG. 6; there are many possible configurations for the tube 24 including a single tube as in FIG. 6*a*, which delivers air to the passive driver 22 from the open end of tube 24 inside the chamber 156. As shown in FIG. 6*b* and FIG. 6*c*, the tube 24 may be made of soft PVC materials, with the addition of evenly distributed holes 244 to allow air pressure to enter the acoustic cavity chamber 156 and pass through the whole chamber in order to provide uniformly distributed air pressure throughout the chamber. The intake tube 24 can include a single branch (as in FIG. 6*b*) or multiple branches (as in FIG. 6*c*).

Additionally regarding FIG. 6*a*, inside the intake tube 24 a flexible solid rod 242 is positioned to prevent the pipe from kinking while allowing for free air flow. As an example, the flexible solid rod 242 may have a diameter of ⅛ of that of the intake tube 24 with the same length as the tube 24, and may also be made of PVC. This flexible solid rod 242 may be fixed inside the tube 24 by means of double sided tape, or another form of suitable adhesive.

Because each of the passive drivers 22 are constructed only of materials which will not perturb magnetic fields, and further because they do not require an electric current to operate, the passive drivers 22 can be freely located anywhere within the bore 12 of the magnet 14. There is no need to align them in any particular direction to operate, and they can be placed very close to the region of interest 10 without producing image artifacts. Further, the flexible nature of the passive drivers 22 provides the ability to conform to various anatomical shapes of the subject 10. This flexible passive driver 22 may also be disposable or designed for only one use with inexpensive but MR compatible materials.

Thus, the present system provides a mechanism for introducing vibrations into abdominal organs, or other body parts of a subject for performing MR elastography or other medical imaging. Specifically, a passive driver is described. The passive driver is configured to communicate vibrational energy generated by an active driver into a subject. For example, a driver may be configured to be placed against the thorax of the subject above, for example, the ribcage to induce a vibration against a wall of the subject's body. The vibration is communicated to the subject's ribcage, which operates as an extension of the passive driver creating cyclic pressure variations across the diaphragm, between, for example, the thorax and abdomen. Shear waves are generated in the abdomen via mode conversion at multiple locations, particularly where the diaphragm contacts upper abdominal organs and at retroperitoneal locations. The system may operate to eliminate unexpected preload to the abdominal organs, further enhancing the reliability of shear stiffness measurements with MRE.

In addition, the system may provide for increased variations in the strength of the trans-diaphragmatic pressure by placing a second passive driver, driven 180 degrees out of phase, against the abdominal wall. In this case, a strap mechanism is placed around the subject to secure the driver to the subject. Using the strap, one or more drivers may be secured to the subject's body at various positions to optimize the location of the drivers depending upon the application. For example, when imaging the kidneys, the strap may be used to position one or more passive drivers to provide optimal energy transfer from the drivers to the kidneys to improve imaging resolution. The system may be used in combination with MR or ultrasound medical imaging.

Figure 3:
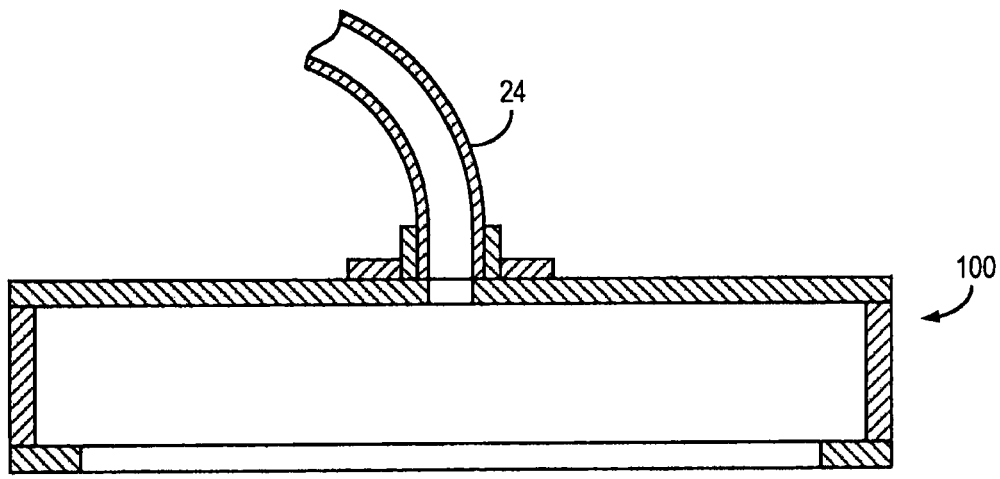
FIG. 3 is a cross-sectional view of a prior art passive driver.

The two passive drivers being used in this configuration may not both be flexible drivers. For example, a flexible driver may be used to deliver vibrational energy to the spleen, while a drum driver like that of the prior art in FIG. 3 may be used to deliver vibrational energy to the liver. Other combinations of driver types may be used with various combinations of organs or regions of interest.

In the same manner as the prior art, the device could be used in other applications including ultrasound, x-ray, other elastography techniques in MRI and other imaging modalities. Accordingly, it will be readily understood by those persons skilled in the art that, in view of the above detailed description of the invention, the present invention is susceptible of broad utility and application. Many adaptations of the present invention other than those herein described, as well as many variations, modifications, and equivalent arrangements will be apparent from or reasonably suggested by the present invention and the above detailed description thereof, without departing from the substance or scope of the present invention.

We claim:

1. An acoustic driver system for producing a stress on a subject undergoing a diagnostic imaging procedure, the acoustic driver system comprising:
    an active driver located remotely from the subject and having a diaphragm operable to produce oscillating acoustic energy by actuating the diaphragm;
    a flexible passive driver positioned on a surface of the subject and having a flexible enclosure which defines an enclosed chamber when placed on the subject, wherein the flexible enclosure has a port for receiving the oscillating acoustic energy, and is filled with a porous three-dimensional structure; and
    an acoustic coupling extending between the active driver and the flexible passive driver to drive the surface of the subject upon which the flexible enclosure rests to vibrate in response to the oscillating acoustic energy produced by the active driver;
    wherein the port connects to a tube disposed inside the enclosed chamber, the tube including an inlet opening for receiving the oscillating acoustic energy and a plurality of holes for delivering the received oscillating acoustic energy from the tube to the enclosed chamber, each of the plurality of holes being distinct from the inlet opening of the tube and oriented within the enclosed chamber.

2. The acoustic driver system as recited in claim 1, wherein the flexible enclosure includes a mesh material configured to inhibit stretching.

3. The acoustic driver system as recited in claim 1, wherein the porous three-dimensional structure is selected from one of polyfiber material, and a non-woven web material configured for cleaning and finishing surfaces.

4. The acoustic driver system as recited in claim 1, wherein the port and the tube disposed inside the enclosed chamber contain a solid support rod.

5. The acoustic driver system of claim 4, wherein the solid support rod permits free air flow within the tube.

6. The acoustic driver system as recited in claim 1, wherein a non-active compartment is coupled with the flexible passive driver and connected with a securing band.

7. The acoustic driver system of claim 6, wherein the non-active compartment restrains vibration of at least one surface of the active flexible passive driver that is removed from the surface of the subject and thereby reflects acoustic energy toward the surface of the subject.

8. The acoustic driver system of claim 6, wherein the non-active compartment is a push-on compartment.

9. The acoustic driver system as recited in claim 1, wherein the plurality of holes are configured to uniformly distribute acoustic energy from the active driver throughout the enclosed chamber.

10. The acoustic driver system as recited in claim 1, wherein the tube disposed inside the enclosed chamber includes first and second branches oriented, at least in part, within the enclosed chamber, each of the first and the second branches including at least one of the plurality of holes.

11. The acoustic driver system as recited in claim 1, wherein the flexible enclosure is formed, at least in part, by material including a two-dimensional mesh of thread.

12. The acoustic driver system of claim 1, wherein the flexible passive driver is sized to cover two or more organs of the subject.

13. An acoustic driver system for producing a stress on a subject undergoing a diagnostic imaging procedure, the acoustic driver system comprising:
    an active driver located remotely from the subject and having a diaphragm operable to produce oscillating acoustic energy by actuating the diaphragm;
    a flexible passive driver including:
        a flexible membrane configured to be positioned on a surface of the subject;
        a plurality of flexible walls connected to the flexible membrane and defining together with the flexible membrane an internal chamber;
        a porous three-dimensional structure substantially filling the internal chamber;
        a port for receiving the oscillating acoustic energy from the active driver and delivering the oscillating acoustic energy to the internal chamber; and
        at least one baffle disposed within the internal chamber; and
    an acoustic coupling extending between active driver and the port to drive the flexible membrane in response to the oscillating acoustic energy produced by the active driver.

14. The acoustic driver system as recited in claim 13, wherein the plurality of walls include a mesh material configured to inhibit stretching.

15. The acoustic driver system as recited in claim 13, wherein the porous three-dimensional structure is selected from one of polyfiber material, and a non-woven web material configured for cleaning and finishing surfaces.

16. The acoustic driver system as recited in claim 13, wherein the port connects to a tube disposed inside the internal chamber, the tube including an inlet opening for receiving the oscillating acoustic energy and a plurality of holes for delivering the received oscillating acoustic energy from the tube to the enclosed chamber, each of the plurality of holes being distinct from the inlet opening of the tube and oriented within the enclosed chamber.

17. The acoustic driver system as recited in claim 13, wherein the flexible passive driver further includes a non-active compartment isolated from the active driver such that the non-active compartment does not receive the oscillating acoustic energy from the active driver.

18. The acoustic driver system as recited in claim 17, wherein the non-active compartment includes a material selected from one of polycarbonates, thermoplastic meshes, woods, foams and other solid MR-compatible materials.

19. The acoustic driver system as recited in claim 13, wherein the at least one baffle includes at least one rod extending from at least one of the flexible membrane and a flexible wall included in the plurality of flexible walls.

20. The acoustic driver system of claim 13, wherein the at least one baffle is surrounded by the porous three-dimensional structure.

* * * * *